(12) United States Patent
Campbell et al.

(10) Patent No.: US 8,979,886 B2
(45) Date of Patent: Mar. 17, 2015

(54) MEDICAL BALLOON AND METHOD OF MAKING THE SAME

(75) Inventors: Carey V. Campbell, Flagstaff, AZ (US); Joel M. Greene, Flagstaff, AZ (US); Lawrence D. Holden, Flagstaff, AZ (US); William Hammond Wiley, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 612 days.

(21) Appl. No.: 11/501,250

(22) Filed: Aug. 7, 2006

(65) Prior Publication Data

US 2008/0033477 A1 Feb. 7, 2008

(51) Int. Cl.
*A61M 29/00* (2006.01)
*A61M 25/10* (2013.01)
*A61L 29/08* (2006.01)

(52) U.S. Cl.
CPC ............ *A61M 25/104* (2013.01); *A61L 29/085* (2013.01); *A61M 25/1029* (2013.01); *A61M 25/1034* (2013.01); *A61M 2025/1031* (2013.01); *A61M 2025/1075* (2013.01); *A61M 2025/1081* (2013.01); *A61M 2025/1084* (2013.01)
USPC ................. 606/192; 604/103.06; 604/103.07; 604/103.08; 604/103.09

(58) Field of Classification Search
CPC .......... A61M 25/104; A61M 25/1029; A61M 25/1034; A61M 2025/1031; A61M 2025/1075; A61M 2025/1081; A61M 2025/1084

USPC ........ 606/192, 194; 604/103.06–103.09, 526, 604/527, 524; 264/512–516
See application file for complete search history.

(56) References Cited

U.S. PATENT DOCUMENTS

| | | | |
|---|---|---|---|
| 4,637,396 A | 1/1987 | Cook | 128/344 |
| 5,116,318 A * | 5/1992 | Hillstead | 604/103.14 |
| 5,201,706 A | 4/1993 | Noguchi et al. | 604/96 |
| 5,330,429 A | 7/1994 | Noguchi et al. | 604/96 |
| 5,476,476 A | 12/1995 | Hillstead | |
| 5,492,532 A | 2/1996 | Ryan et al. | |
| 5,653,689 A | 8/1997 | Buelna et al. | |
| 5,868,779 A | 2/1999 | Ruiz | |
| 6,120,477 A * | 9/2000 | Campbell et al. | 604/96.01 |
| 6,156,254 A | 12/2000 | Andrews et al. | 264/231 |
| 6,746,425 B1 * | 6/2004 | Beckham | 604/103.09 |
| 2002/0045017 A1 | 4/2002 | Wang et al. | |
| 2002/0161388 A1 | 10/2002 | Samuels et al. | 606/192 |
| 2004/0082965 A1 | 4/2004 | Beckham | 606/192 |
| 2004/0109964 A1 | 6/2004 | Beckham | 428/35.9 |
| 2005/0123702 A1 | 6/2005 | Beckham | 428/363 |
| 2005/0271844 A1 * | 12/2005 | Mapes et al. | 428/36.1 |
| 2006/0004399 A1 * | 1/2006 | van Ockenburg et al. | 606/192 |
| 2006/0085022 A1 * | 4/2006 | Hayes et al. | 606/192 |
| 2006/0111649 A1 * | 5/2006 | Zhou | 600/585 |

FOREIGN PATENT DOCUMENTS

| | | |
|---|---|---|
| EP | 0 102 422 | 7/1987 |
| EP | 0 959 937 | 11/2003 |
| WO | 98/05377 | 2/1998 |

* cited by examiner

*Primary Examiner* — Darwin Erezo
*Assistant Examiner* — Katrina Stransky
(74) *Attorney, Agent, or Firm* — David J. Johns (57) ABSTRACT

Reinforced angioplasty balloon having an external elastic sheath. The elastic sheath maintains, along its length, a substantially uniform circular cross-section during balloon inflation and forces a deflated balloon into a compacted, substantially circular, wingless profile.

37 Claims, 7 Drawing Sheets

MEDICAL BALLOON AND METHOD OF MAKING THE SAME

BACKGROUND OF THE INVENTION

1. Field of the Invention

This invention relates generally to medical devices and methods of making the same. More particularly the invention relates to balloons for use in medical applications, such as balloons for use with catheters.

2. Discussion of the Related Art

As an alternative to open-heart, coronary bypass surgery, a technique referred to as coronary transluminal angioplasty has been developed. In carrying out this procedure, a dilatation catheter having a balloon on the distal end is routed through the vascular system to a location within a coronary artery containing a stenotic lesion. Following placement of the balloon across the lesion, a fluid is introduced into the proximal end of the catheter and is used to inflate the balloon to a predetermined relatively high pressure whereby the lesion is compressed into the vessel wall restoring patency to the previously occluded vessel.

In conventional stent deploying balloon catheters, the balloon is made of essentially non-compliant material, such as nylon or polyethyleneterephthalate (PET). Such non-compliant material exhibits little expansion in response to increasing levels of inflation pressure. Because the non-compliant material has a limited ability to expand, the uninflated balloon must be made sufficiently large so that, when inflated, the balloon has sufficient working diameter to compress the stenosis and open the patient's passageway. However, a large profile, non-compliant balloon can make the catheter difficult to advance through the patient's narrow vasculature because, in an uninflated condition, such balloons form flat or pancake shaped wings which extend radially outward. Consequently, the wings of an uninflated balloon are typically folded into a low profile configuration for introduction and advancement through the vessel. The wings are again produced upon deflation of the balloon following stent deployment within the patient. These wings on the deflated balloon are undesirable because they result in an increased balloon profile which can complicate withdrawing the catheter after stent deployment.

Although stents have been used effectively for some time, the effectiveness of a stent can be diminished if it is not properly implanted within the vessel. For example, expansion of a balloon folded into a low profile configuration for introduction into the patient, can cause non-uniform expansion of a stent mounted on the balloon.

The non-uniform expansion of conventional designs has resulted in the use of an elastic sleeve around the balloon and under the stent to uniformly distribute force from the expanding folded balloon to the stent. Additionally, such an elastic sleeve can encourage the inflated balloon to deflate into a "wingless", compact profile.

In many interventional radiology practices, a common indication for balloon angioplasty is for treatment of neointimal hyperplastic stenoses associated with hemodialysis grafts and fistulas. Unlike softer atherosclerotic stenoses, these neointimal hyperplastic lesions can be difficult to dilate and require the use of ultra-high pressure angioplasty balloons, capable of sustaining pressures up to 30 atm.

SUMMARY OF THE INVENTION

Accordingly, the present invention is directed to a medical balloon and method of making the same that substantially obviates one or more of the problems due to limitations and disadvantages of the related art.

The present invention comprises a medical balloon comprising: a fiber reinforced balloon at least partially surrounded by an elastomeric sheath.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE INVENTION

Reference will now be made in detail to embodiments of the invention, example of which is illustrated in the accompanying drawings.

Figure 1:
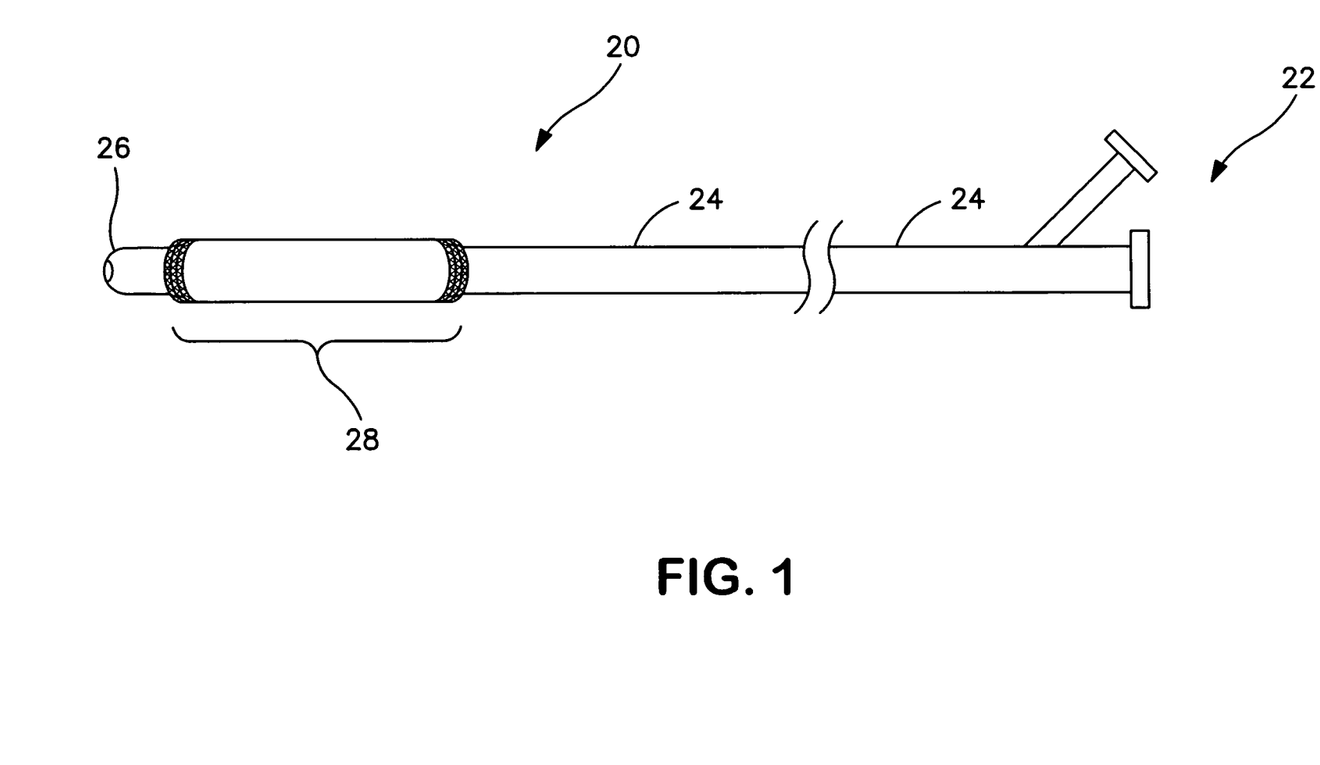
FIG. 1 is a perspective view of a catheter assembly of the present invention showing a balloon catheter having a externally sheathed balloon.

FIG. 1 illustrates a perspective view of a catheter assembly 20. The catheter assembly 20 includes a proximal hub assembly 22, a catheter body 24, which terminates at a distal catheter tip 26. Proximal to the distal catheter tip 26 is a balloon and elastomeric sheath portion 28 according to the invention.

Figure 2:
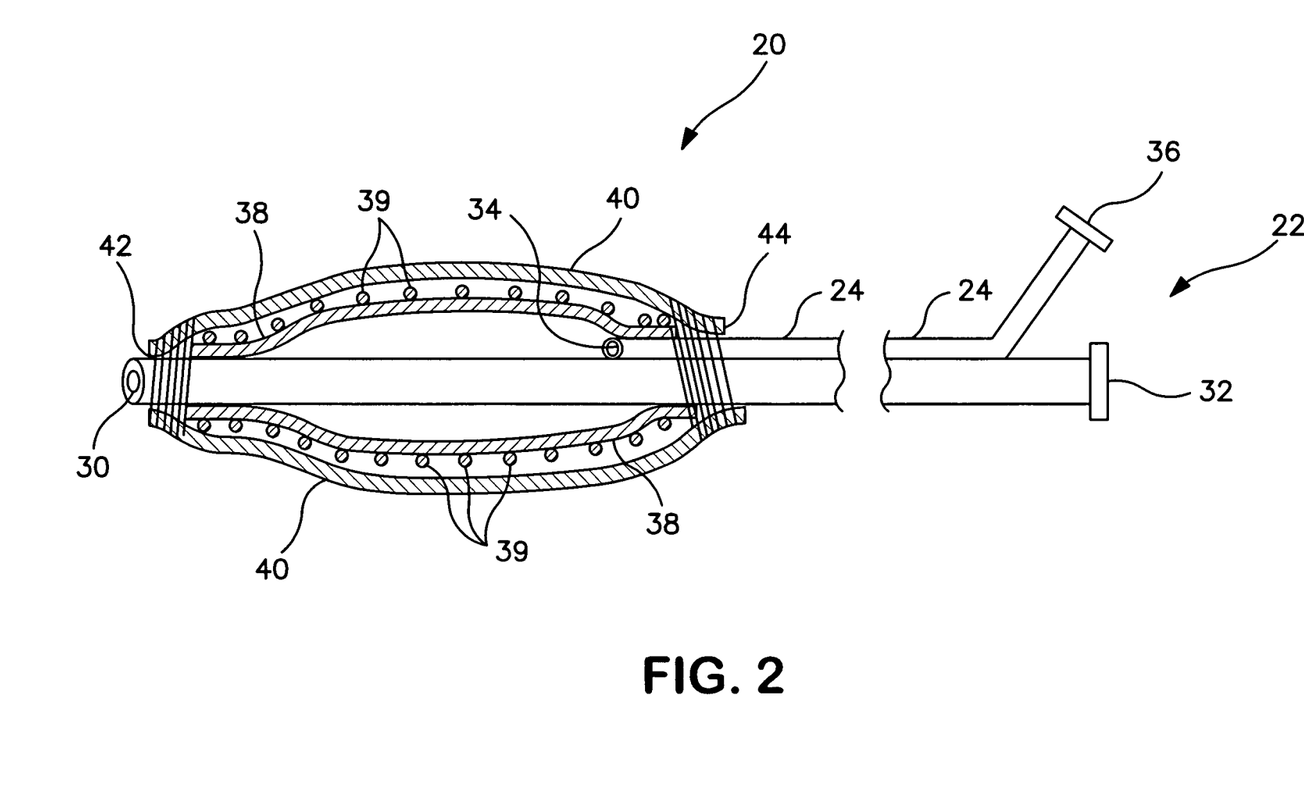
FIG. 2 is a cross-sectional view of the catheter assembly, detailing the distal balloon portion.

FIG. 2 illustrates a cross-sectional view of the catheter assembly 20. Referring to the catheter assembly 20 illustrating an over-the-wire balloon catheter as known in the art including a distal guidewire port 30. A guidewire lumen extends from the distal port 30 through the length of the catheter and terminates proximally at the hub port 32. Similarly, an inflation lumen has a distal port 34 and extends the length of the catheter, terminating at the proximal hub port 36. Referring now to the balloon and elastomeric sheath portion 28, this portion includes a balloon wall 38, reinforcing fibers 39, and an elastomeric sheath wall 40. The elastomeric sheath can be attached to the distal end of the catheter e.g., by an adhesive film wrap 42. The proximal end of the elastomeric sheath can be attached to the catheter e.g., by an adhesive film 44. Other suitable attachment techniques may also be used.

Figure 3:
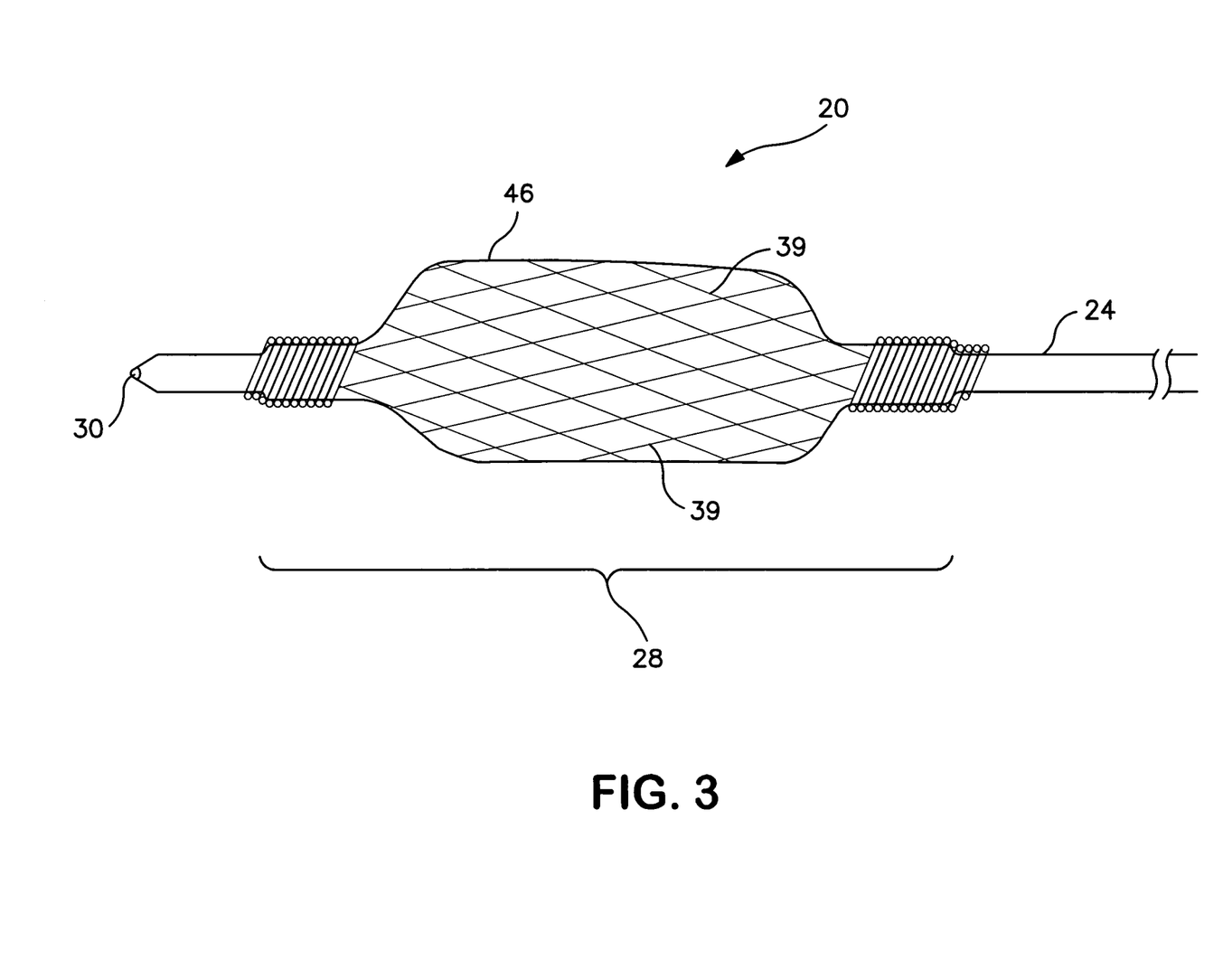
FIG. 3 is a partial side-view of a catheter assembly showing the balloon and elastic sheath in an expanded state.

FIG. 3 illustrates a partial side-view of a catheter assembly 20 depicting the balloon and elastomeric sheath 28 in an expanded state. Referring to FIG. 3, shown are distal guidewire port 30, catheter body 24 and the expanded elastomeric sheath 46. Fibers 39 are positioned on the exterior surface of the underlying balloon (not shown).

Figure 4A:
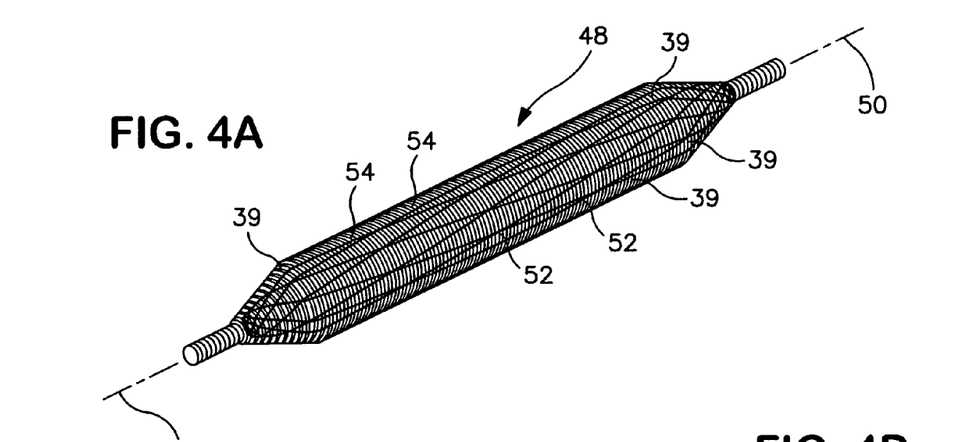
FIGS. 4A and 4B show isometric and side views of a fiber reinforced balloon of the present invention, detailing various filament winding patterns that define angular off-sets.
Figure 4B:
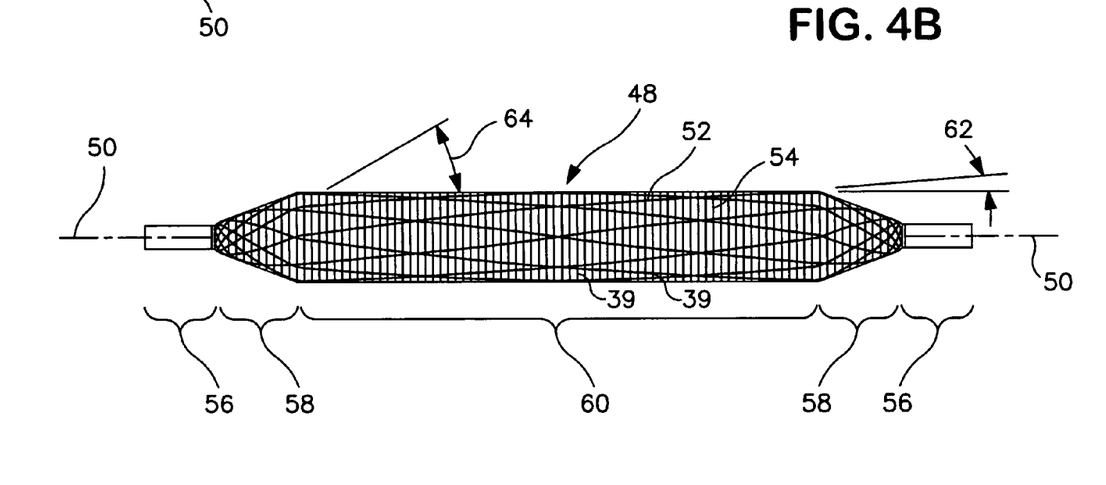

FIGS. 4A and 4B illustrate isometric and side views, respectively of a fiber reinforced balloon of the invention. Referring to FIG. 4A, a balloon is generally depicted as 48 and includes a longitudinal axis 50 and fiber reinforcements 39. The fiber reinforcement 39 is shown having two distinct wrapped patterns. Other wrapping patterns as known in the art may also be used. In this embodiment, a first wrapped pattern has a generally longitudinal spiral configuration 52. For example, the fibers are arranged such that they are substantially aligned with a longitudinal axis of the balloon. These fibers may have an angular off-set relative to the longitudinal balloon axis 50. Also shown is a second wrapped pattern 54, this pattern is generally circumferential to the balloon and substantially perpendicular to the longitudinal axis 50 of the balloon. Other wrapping patterns may also be used. This generally circumferential, helical pattern is commonly referred to as a "hoop wrap".

Referring to FIG. 4B illustrating a side view of the balloon of FIG. 4A, the balloon 48 has two opposed leg portions 56 that are joined or integral to opposing shoulder portions 58 that define a balloon body portion 60. Across the surface of the balloon 48 is a first wrapped pattern having a generally longitudinal spiral configuration 52. For example, the fibers are arranged such that they are substantially aligned with a longitudinal axis 50 of the balloon 48. These fibers may have an angular off-set relative to the longitudinal balloon axis 50. This angular off-set is depicted as 62 and generally defines an angle between the balloon longitudinal axis 50 and the spiral wrapped fibers 52, along the balloon body portion 60. Similarly, an angular off-set is depicted as 64 and generally defines the angle between the balloon longitudinal axis 50 and the spiral wrapped fibers 52, along the balloon shoulder portion 58. Also shown is a second wrapped pattern, the fibers 54 of this pattern are generally circumferential to the balloon and substantially perpendicular to the longitudinal axis of the balloon. Fibers 54 are shown with an angular off-set of about 90° to the longitudinal balloon axis 50. Again, other patterns may also be used.

Figure 5A:
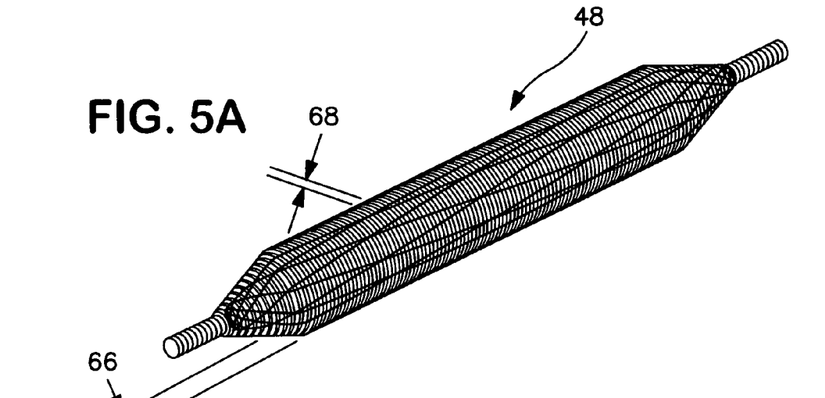
FIGS. 5A and 5B show isometric and side views of a fiber reinforced balloon of the present invention, detailing various filament winding patterns that define filament to filament spacings.
Figure 5B:
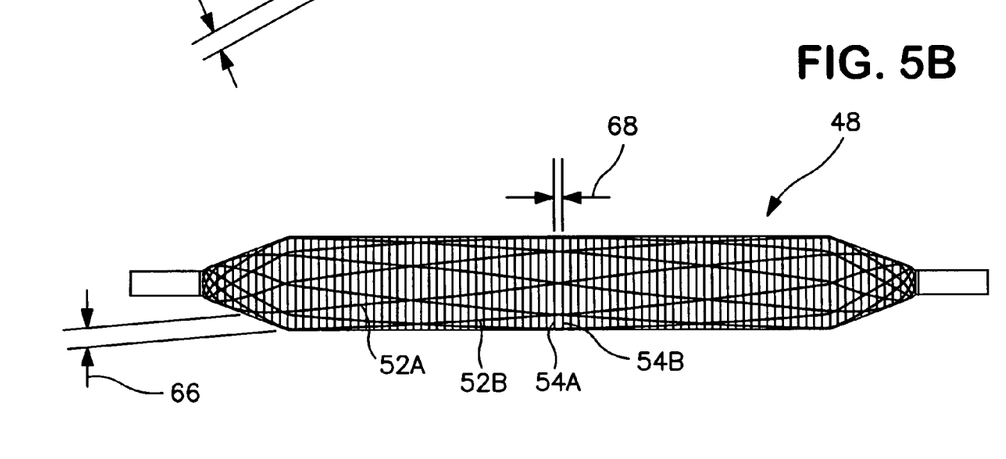

FIGS. 5A and 5B illustrate isometric and side views, respectively, of a fiber reinforced balloon of the present invention having two generally distinct reinforcement patterns. Shown in FIG. 5A is an approximate spacing 66 between two adjacent longitudinal spiral wrapped fibers. Similarly shown is an approximate spacing 68 between two adjacent hoop wrapped fibers.

As shown in FIG. 5B, two adjacent longitudinal fibers 52A and 52B define an approximate spacing 66 between the two fibers. Two adjacent hoop wrapped fibers 54A and 54B define an approximate spacing 68 between the two fibers. Both of the fiber spacing 66 and 68 apply to the body portion of the balloon.

The fiber reinforced balloons of the invention can be configured in a variety of ways and can be fiber wrapped with a specific pattern to suit a particular balloon application. For example, the angular off-set 62 between the balloon longitudinal axis 50 and the spiral wrapped fibers 52, along the balloon body portion 60, can be varied. For example, the angular off-set 62 can be in a range from about 1° to about 45°. In an aspect of the invention the angular off-set can be in a range of about 1° to about 10°. In a further aspect of the invention the angular off-set can be in a range of about 4.5° to about 5.5°. Hoop wrapped fibers 54 can also have a variety of angular off-sets relative to the longitudinal balloon axis 50. This hoop wrapped angular off-set (relative to the balloon longitudinal axis) can be in the range from about 45° to about 90°. In an aspect of the invention the angular off-set can be in the range of about 85° to about 90°. In a further aspect of the invention the angular off-set can be in the range of about 89° to about 89.9°.

In addition, the spacing 66 (FIG. 5B) between two adjacent longitudinal fibers can also be varied. For example, the spacing 66 between two adjacent longitudinal wrapped fibers 66 can range from about zero to about 20 mm. In an aspect of the invention the spacing between wrapped fibers 66 can range from about 0.1 mm to about 2 mm. In a further aspect of the invention the spacing between wrapped fibers 66 can range from about 0.2 mm to about 0.6 mm. The spacing does not need to be constant between all longitudinal fibers 66.

Moreover, the approximate spacing 68 (FIG. 5B) between two adjacent hoop wrapped fibers can also be varied. For example, the approximate spacing 68 between two adjacent hoop wrapped fibers can be range from about zero to about 20 mm with a preferred range of about 0.1 mm to about 0.3 mm, with a most preferred range of about 0.15 mm to about 0.2 mm.

The fiber material used for wrapping can be comprised of any suitable flexible strand possessing high-strength and minimal elongation as known in the art. In an aspect of the invention a high-strength fiber can have a tensile strength ranging from about 0.5 Gpa to about 2.5 Gpa (or even higher), and can have an elongation to break of less than about 5%. For example the fibers can be polyethylene fiber, polyimide fiber, liquid crystal polymer fiber, carbon based fiber, such as Kevlar® fiber, metal fiber, such as stainless steel, alloy fiber, such as nitnol, and combinations thereof.

The fibers can also have varied diameters and/or cross-sections. For example, the fibers can have a circular cross section with a diameter ranging from about 0.0001 mm to about 1 mm. In an aspect of the invention the fibers can have a circular cross section of about 0.01 mm to about 0.1 mm. In a further aspect of the invention the fibers can have a circular cross section of about 0.03 mm to about 0.05 mm. In addition, the fibers can have a non-circular cross-section, such as, for example, a triangle, rectangle, square and other geometric shape. Moreover, the geometry of the fibers may be the same or varied. For example, the hoop fibers may be a substantially flat cross-section, while the longitudinal fibers may have a substantially circular cross-section. In addition, a first wrapping of the hoop fibers may have a substantially flat cross-section while a second portion may have a substantially circular cross-section.

The balloon material may be any suitable material. For example, the balloon material may be generally elastic or generally non-elastic. By way of example, generally elastic balloon materials may include polyurethanes, latex and elastomeric organosilicone polymers, such as, polysiloxanes. Also, for example, inelastic balloon materials may include polymers and copolymers used in medical balloons as known in the art. The material of an inelastic balloon may be, for example, polyethylene, polyethylene terephthalate (PET), polycaprolactam, polyesters, polyethers, polyamides, polyurethanes, polyimides, ABS copolymers, polyester/polyether block copolymers, ionomer resins, liquid crystal polymers and rigid rod polymers. The balloon profile may also be configured to suit any particular application. In addition, the balloon profile can include a variety of configurations for the leg portions, shoulder portions, body portion, diameters and wall thicknesses.

Various combinations of wrapping patterns can be applied to the balloons. For example, wrapping patterns can be varied within a single wrapping pass to vary the wrap pattern along the balloon length. A specific wrapping pattern can be maintained along a single pass and then altered on subsequent passes. The longitudinal as well as the hoop wrap patterns may also be varied. Different fiber materials or configurations, e.g., tapes, ribbons and circular fibers, can be used on individual passes and can be combined with different fiber materials or configurations on subsequent passes.

The balloon, when combined with an elastomeric sheath maintains, along its length, a substantially uniform circular cross-section during inflation and deflates to a compacted, substantially circular, wingless profile. The elastomeric sheath has a low degree of radial strength and high degree of longitudinal strength. The sheath may be selected from materials such it has a low degree of radial strength and a high degree of longitudinal strength. For example, the elastomeric sheath may be made from expanded polytetrafluoroethylene where the tube is dipped into an elastomeric solution. Also, the elastomeric sheath may also be reinforced with fibers as described herein throughout.

Figure 6:
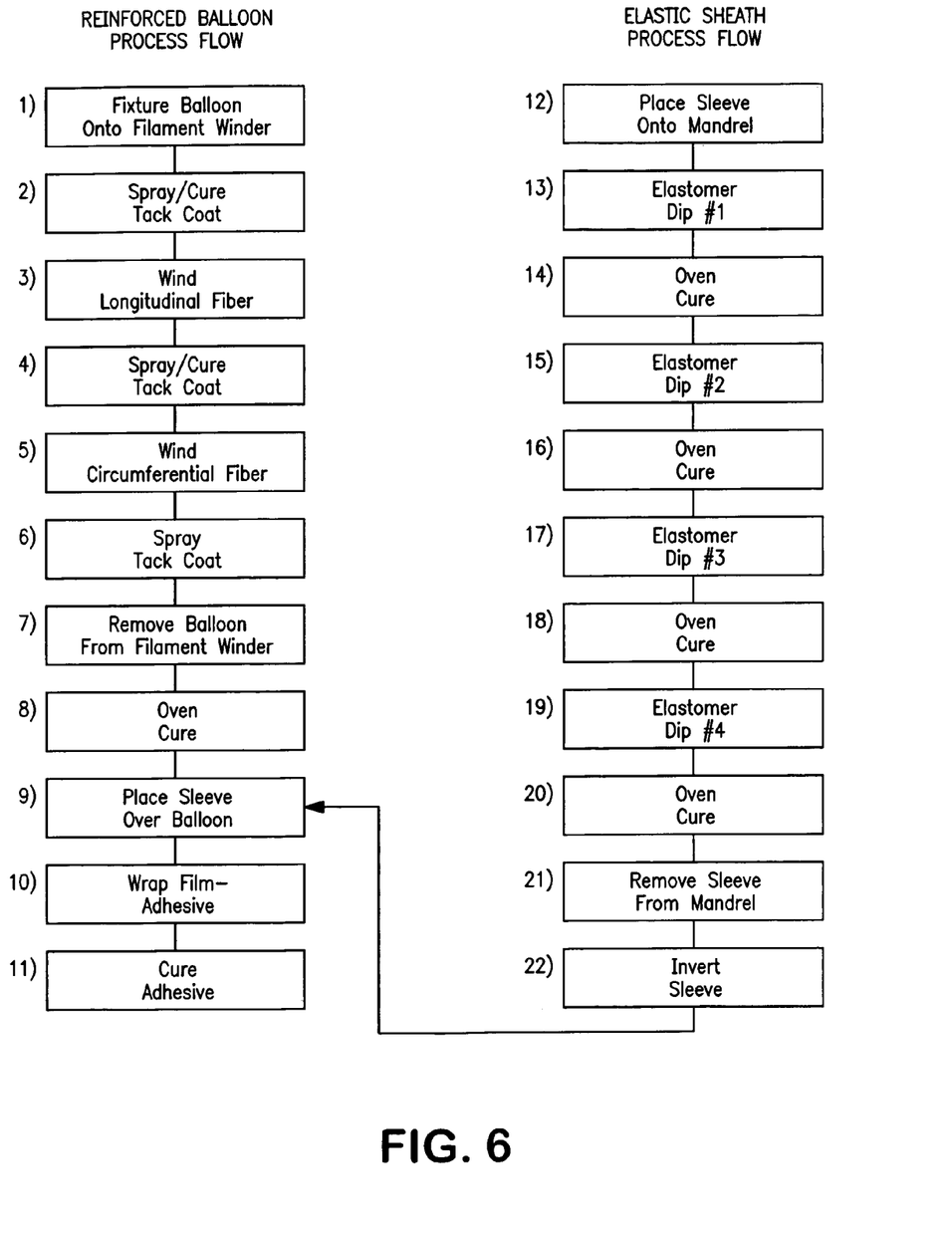
FIG. 6 is a process flow chart showing a detailed method of manufacture for a reinforced balloon along with an elastomeric sheath.

FIG. 6 is a process flow chart for fabrication of a non-complaint medical balloon along with an external elastomeric sheath according to an embodiment of the invention. The following paragraphs detail each step:

1. An over the wire catheter having a non-elastic balloon can be positioned onto a multi-axis filament winding machine. Conventional balloon catheters as known in the art may be used. A stiffening wire, e.g., steel wire, or mandrel can be threaded through the guidewire lumen of the catheter so that approximately 10 cm or other suitable length of the wire extends from both ends of the catheter. The stiffening wire can be joined to the catheter proximal end, e.g., hub by tightening the catheter's Tuohy-Borst compression fitting as known in the art. The opposite end, i.e., distal end of the catheter can be joined to the stiffening wire by pre-wrapping a thin film of tape, e.g., pipe thread tape onto the stiffening wire. This tape build-up should cause a slight interference fit between the wire and the distal end of the catheter. Adhesives or adhesive tapes can also be used as known in the art. The stiffening wire can then be clamped into the filament winders two opposing rotating collets. The collet adjacent to the proximal (hub) end of the catheter can then be driven away from the catheter distal end, thereby applying tension to the stiffening wire. The catheter inflation port can then be connected to the proximal collet of the filament winder and the balloon inflated to its nominal diameter.

2. A tack coat can then be applied to the inflated balloon. This tack coat allows a low tensioned filament to remain seated against the balloon during winding. As the balloon is slowly rotated by the filament winder, a spray, e.g., a mist of tacking, e.g., of BioSpan segmented polyurethane, part # FP70001 (from PTG Medical LLC) can be applied to the balloon. The spray mist may also be applied to the catheter portions extending about 10 cm beyond the balloon legs. The tack coat can then be pre-cured, for example, the coating may be heated by heating devices as known in the art. For example, a convection air blower may be used to cure the coating.

3. A fiber can then be wound onto the balloon in a longitudinal pattern, such as is shown in FIGS. 4A and 4B. A filament or fiber may be spooled onto the winder and threaded through a tensioning system. For example, servo controlled "closed-loop pay-out" systems can be used in place of conventional "open-loop tensioning systems" as known in the art. The filament or fiber may be fixed to the catheter by wrapping the filament around the catheter distal to the balloon in a circumferential pattern. The fiber can be progressively wound onto the balloon and catheter throughout several pre-programmed, machine controlled passes. For example, a first pass may start at a position distal to the balloon and terminate at a position proximal to the balloon. The next pass may be reversed, that is, starting proximal to the balloon and terminated distal to the balloon. Accordingly, at least two longitudinal fibers may be comprised of a single, continuous fiber. The pre-programmed passes are continued until the programmed amount of passes is complete.

Figure 7:
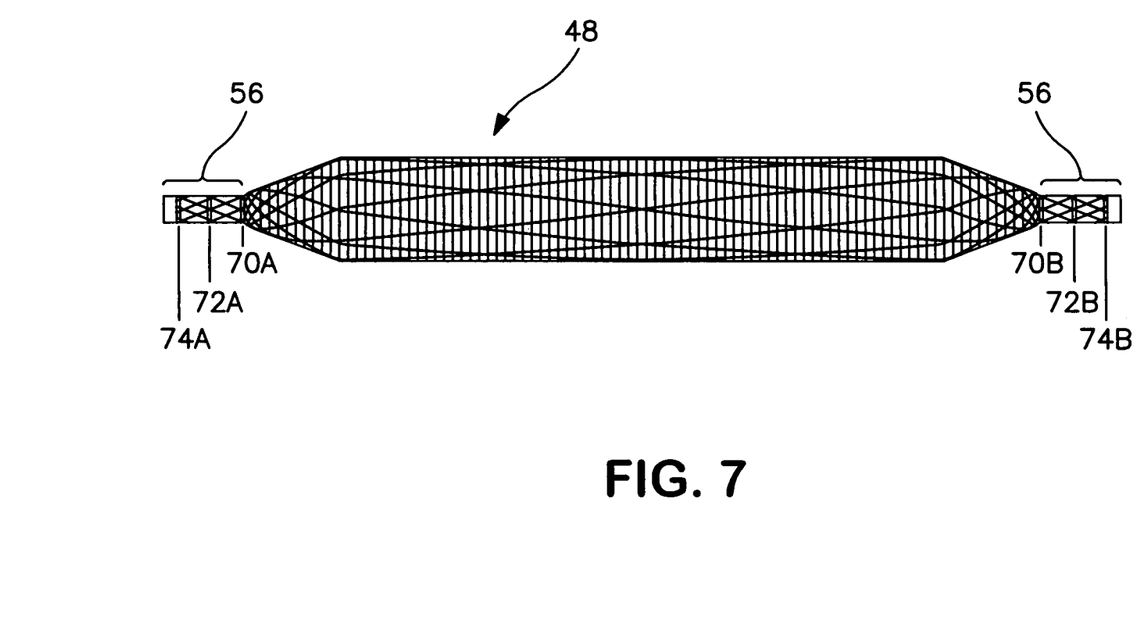
FIG. 7 is a side view of a filament reinforced balloon showing varied turn-around points used in a filament winding pattern.

To minimize fiber buildup at the two opposed reversal or turn-around points, the winding program can incorporate progressively varied turn-around points. Referring to FIG. 7, the balloon 48 has two opposed leg portions 56. Paired turn-around points 70A and 70B, 72A and 72B, 74A and 74B are illustrated. A left to right pass may initiate at point 70A, such a pass terminates and may have a turn around at point 70B. In the next pass to the left the turn around point may be 72A. The next pass to the right terminates and turns around at point 72B, continuing to the left and may terminate at point 74A. The subsequent pass to the right may terminate at point 74B. This pattern of progressively varied turn-around points can be continued until the balloon is completely wound. Accordingly, the turn around points may successively extend a distance further from the previous point of reversal, thereby avoiding build-up at the two opposed end regions. Moreover, this method of successively varying turn-around points in order is particularly suited to automated fiber winding balloon configurations.

4. A second tack coat may be applied to the inflated balloon and catheter and then pre-cured by the process defined in previous step 2. If desired, the fiber can be terminated by first attaching the fiber to the catheter by a series of circumferential wraps, prior to the application of the tack coat. After application and curing of the tack coat, the fiber can then be cut.

5. A fiber may then be wound onto the balloon in a circumferential or hoop pattern. The filament or fiber may be spooled onto the winder used in previous step 3 and threaded through the tensioning system. The filament can be fixed to the catheter by wrapping the filament around the catheter distal to the balloon in a pattern, e.g., a helical pattern. The fiber may be progressively wound onto the balloon and catheter throughout pre-programmed patterns. For example, a first pass may start at a position distal to the balloon and terminate at a position proximal to the balloon. The next pass may be reversed, that is, it may start proximal to the balloon and terminate to the distal end of the balloon. The pre-programmed passes may be continued until the programmed amount of passes is complete.

6. Another tack coat may be applied to the inflated balloon and catheter by the process defined in previous step 2. This tack coat can be final cured in a subsequent process step. Prior to applying the tack coat the fiber can be attached to the catheter by a series of circumferential wraps and then cut.

7. The balloon catheter can then be removed from the filament winder by detaching the catheter inflation port and releasing the machine collets to free the stiffening wire.

8. The balloon catheter can be cured as known in the art. For example, the catheter may be placed into an air convection oven to cure the tack coats.

9. The balloon from prior step 8 incorporates an external elastomeric sheath. The elastomeric sheath permits the balloon to maintain a substantially uniform circular cross-section, along its length during inflation. In addition, the elastomeric sheath enables a compacted, substantially circular and wingless profile at and during deflation. To place a previously manufactured elastomeric sheath over the fiber reinforced balloon, the reinforced balloon can be initially folded into a compacted shape. The folded balloon can be inserted into an introducer sheath. The conventional introducer sheath can have on the proximal end a hemostatic valve and a flushing port/valve. The balloon can be advanced through the hemostatic valve and positioned within the introducer sheath near the distal end of the sheath. One end of the elastomeric sheath is then placed over the distal end of the introducer sheath. The elastomeric sheath can then be clamped and sealed onto the introducer sheath by the use of a conventional Tuohy-Borst compression fitting. The other end of the elastomeric sheath can then be closed and sealed by the use of a conventional hemostatic locking clamp. Once the elastomeric sheath is affixed and sealed to the introducer sheath, an inflating fluid can be injected into the introducer inflation port. Since the balloon catheter shaft is sealed by the hemostatic valve and the elastomeric sheath is closed and sealed to the introducer sheath, the inflating pressure will cause the elastomeric sheath to expand. After the elastomeric sheath is appropriately expanded, the balloon can be advanced and inserted into the expanded elastomeric sheath. The inflation pressure can then be bled-off, allowing the elastomeric sheath to deflate and retract down upon the compacted balloon.

10. To secure the sheath to the balloon legs, for example, a film wrapping and a UV curable adhesive can be applied to the ends of the elastomeric sheath. Any other suitable thin film, e.g., expanded polytetrafluoroethylene may be wrapped under tension onto the ends of the elastomeric sheath. The film wrapping compresses the elastomeric sheath down onto the balloon leg portions. A suitable UV curable adhesive can then be applied onto the wrapped film.

11. The covered balloon can then be placed under cured as known in the art. For example, a UV source may be used to cure the adhesive, thereby resulting in a fiber reinforced medical balloon covered by a sheath as generally shown in Figures herein throughout.

12. The sheath used in prior process step 9 may be manufactured by initially placing a tube of expanded polytetrafluoroethylene (ePTFE) over a mandrel. The longitudinally extruded and expanded tube has a relative high degree of longitudinal strength and a relatively low degree of radial strength. Such a tube will therefore expand radially and resist longitudinal extension. The sleeve can be, for example, a tube with a thin wall, for example, a wall ranging from about 0.008 mm to about 0.05 mm. The uninflated outer diameter of the tube can range from about 0.5 mm to about 10 mm or greater. For example, the tube may have an outer diameter ranging from about 0.5 mm to about 20 mm or greater. In an aspect of the invention the tube length can be about 25 cm and can be any length compatible with the subsequent dipping process and desired balloon length. The mandrel is preferably slightly undersized to the tube inner diameter. For example, a tube with an outer diameter of about 1 mm with a wall thickness of about 0.02 mm may have an inner diameter of about 0.06 mm. A slightly undersized mandrel may therefore have an outer diameter of about 0.05 mm. After placing the tube onto the mandrel, the tube can be hand smoothed to remove any wrinkles. One end of the tube may protrude over one end of the mandrel and the overhanging tube end can be twisted to help secure the tube onto the mandrel.

13. The mandrel and surrounding tube may be dipped and imbibed into an elastomer solution. Any suitable elastomeric dispersion can be used as known in the art. A typical suitable solution comprises BioSpan® (segmented polyurethane, 24%±2% solids content; from PTG Medical LLC, part number FP70001, Berkeley Calif. 94710) which is diluted to about 12% (weight percent) solids content using dimethylacetamide (DMAC; from Sigma-Aldrich, part number D5511, St. Louis Mo.). The elastomer solution is preheated to about 40-80° C. in an appropriately sized test tube. The preheat temperature and preheat times as well as the solution solids content can be varied as known in the art. The test tube with the preheated solution can then be fixtured into a dipping fixture. The dipping fixture may include a servo-driven vertical cross-head with a clamping device suited to clamp and hold the mandrel in a vertical position with the wrapped end of the tube pointing down. The servo-driven cross-head may be configured to descend and progressively submerge the mandrel and tube into the elastomer solution. A typical descent rate may be about 0.1-2 cm/second, this may vary as known in the art. About 15 cm of the tube may be submerged and held in the submerged position for a dwell time of about 10 to about 90 seconds or other submersion times as known in the art. The cross-head is then raised with an assent rate of about 0.1 to 2 cm/second, which may vary as known in the art, until the lower end of the mandrel and tube is removed from the elastomeric solution and test tube. Descent and assent rates as well as dwell times can be varied to control the amount of elastomer imbibed and coated onto the tube.

14. The mandrel with the dipped tube can then be removed from the dipping fixture and cured. For example, they may be placed into an air convection oven at about 50-80° C. for about 1 to 3 minutes, of course other cure times and temperatures may be utilized as known in the art.

15. The mandrel and tube can then be re-dipped and imbibed according to the previous step 13.

16. The mandrel and dipped tube can then be pre-cured according to the previous step 14.

17. The mandrel and tube can then be re-dipped and imbibed according to the previous step 13.

18. The mandrel and dipped tube can then be pre-cured according to the previous step 14.

19. The mandrel and tube can then be re-dipped and imbibed according to the previous step 13.

20. The mandrel and dipped tube can then be removed from the dipping fixture and placed into an air convection oven. The mandrel and dipped tube can then be final-cured at about 50-80° C. for about 45 to about 90 minutes. The resulting elastomeric tube forms a sheath that is radially expandable and resists longitudinal stretching.

21. The final cured tube/sheath can then be removed from the mandrel, and cut to a length that is approximately equal to the length of the desired balloon. Referring to FIG. 4B, a typical balloon length consists of a balloon body, two opposing balloon ends and two opposing balloon legs. The overall cut length of the elastomeric sheath may be configured to cover the balloon body, both tapered ends and at least a portion of the two balloon legs.

22. The elastomeric sheath can then be inverted. Since the elastomeric layers were built up on the external surface of the starting ePTFE thin walled tube, the inner surface of the sheath has a lubricious, primarily ePTFE surface. By inverting the sheath, the lubricious surface is now on the exterior of the sheath. The inverted sheath can then be optionally placed over a reinforced balloon according to process step 9 above.

EXAMPLES

Example 1

A preferred embodiment of a high-pressure, non-elastic balloon having a fiber reinforcement and an external elastomeric sheath is detailed in Example 1. This example follows the process flow outlined according to FIG. 6.

1. An over the wire catheter having a non-elastic balloon of PET with an inflated body diameter of about 8 mm, a body length of about 40 mm, shoulder lengths of about 18 mm (20° included angle), leg lengths of about 7 mm and leg diameters of about 1.4 mm (from Advanced Polymers Inc., N.H.), was positioned onto a mult-axis filament winding machine. A stiffening wire or mandrel was threaded through the guidewire lumen of the catheter so that approximately 10 cm of the wire extended from both ends of the catheter. The stiffening wire was joined to the catheter proximal end (hub) by tightening the catheter's Tuohy-Borst compression fitting. The opposite, distal end of the catheter was joined to the stiffening wire by pre-wrapping the wire with an ePTFE film. This film buildup caused an interference fit between the wire and the catheter. The stiffening wire was then clamped into the filament winder's two opposing rotating collets. The collet adjacent to the proximal (hub) end of the catheter was then driven away from the catheter distal end, thereby applying tension to the stiffening wire. The catheter inflation port was connected to the proximal collet of the filament winder and the balloon was then inflated to its nominal diameter.

2. A tack coat was then applied to the inflated balloon. As the balloon was slowly rotated by the filament winder, a spray mist of BioSpan segmented polyurethane, part # FP70001 (from PTG Medical LLC) was applied to the balloon leg, shoulder and body portions. The spray mist was also applied to the catheter portions extending about 10 cm beyond the balloon legs. The tack coat was then pre-cured by a heated convection air blower (approximately 70° air temperature) as the balloon continued to rotate.

3. A fiber was then wound onto the balloon in a longitudinal spiral pattern, substantially as shown in FIGS. 4A and 4B. A liquid crystal polymer fiber about 0.04 mm in diameter (from Ceianese Advanced Materials, Charlootte, N.C. Material 25/5 HS, 25 denier) was spooled onto the winder and threaded through a servo controlled "closed-loop pay-out" system to control the tension. The filament was then fixed to the catheter by wrapping the filament around the catheter distal to the balloon in a circumferential pattern. The fiber was then progressively wound onto the balloon and catheter throughout 64 pre-programmed, machine controlled passes.

To minimize fiber buildup at the two opposed "reversal" or turn-around points, the winding program incorporated progressively varied turn-around points as previously described and shown in FIG. 7.

4. A second tack coat was then applied to the inflated balloon and catheter and then pre-cured by the process defined in previous step 2. The fiber was terminated by first attaching the fiber to the catheter by a series of circumferential wraps and then cut, thus allowing the balloon to rotate during application of the mist tack coat.

5. The fiber was then wound onto the balloon in a circumferential or "hoop" pattern, substantially as shown in FIGS. 4A and 4B (Item 54) for an example of a "circumferential pattern". The fiber was spooled onto the winder used in previous step 3 and threaded through the tensioning system. The filament was then fixed to the catheter by wrapping the filament around the catheter distal to the balloon in a circumferential pattern. The fiber was then progressively wound onto the balloon and catheter through the pre-programmed, machine controlled passes, resulting in about 155 turns/inch.

6. A third tack coat was then applied to the inflated balloon and catheter by the process defined in previous step 2. Prior to applying the tack coat the fiber was attached to the catheter by a series of circumferential wraps and then cut.

7. The balloon catheter was then removed from the filament winder by detaching the catheter inflation port and releasing the machine collets to free the stiffening wire.

8. The balloon catheter was then placed into an air convection oven set to about 70° C. and the tack coats were final cured for about 15 minutes.

9. A previously manufactured sheath was then placed over the fiber reinforced balloon. The sheath was manufactured as detailed in process steps 12 through 22 herein. The reinforced balloon was initially folded into a compacted shape. The folded balloon was inserted into a 7Fr introducer sheath. The conventional introducer sheath had on the proximal end a hemostatic valve and a flushing port/valve. The balloon was advanced through the hemostatic valve and positioned within the introducer sheath near the distal end of the sheath. One end of the elastomeric sheath was then placed over the distal end of the introducer sheath. The elastomeric sheath was then clamped and sealed onto the introducer sheath by the use of a conventional Tuohy-Borst compression fitting (Large Diameter Part #11183, from Qosina, Edgewood, N.Y.). The other end of the elastomeric sheath was then closed and sealed by the use of a conventional hemostatic locking clamp. Once the elastomeric sheath was affixed and sealed to the introducer sheath, an inflating fluid was injected into the introducer inflation port causing the elastomeric sheath to expand. After the elastomeric sheath was appropriately expanded to about 4 mm, the balloon was advanced and inserted into the expanded elastomeric sheath. The inflation pressure was then bled-off, allowing the elastomeric sheath to deflate and retract down upon the compacted balloon.

10. To secure the sheath to the balloon legs, a film wrapping and a UV curable adhesive was applied to the ends of the elastomeric sheath. An ePTFE thin film was wrapped under tension onto the ends of the elastomeric sheath. The film wrapping compressed the elastomeric sheath down onto the balloon leg portions. A UV curable adhesive (Grade 3381 from Loctite) was then applied onto the wrapped film.

11. The covered balloon was then placed under a UV source to cure the adhesive, resulting in a non-compliant, fiber reinforced balloon covered by an elastomeric sheath as generally shown in FIG. 2. Referring to FIG. 4B, the shoulder angle off-set 64 was about 6° relative to the longitudinal balloon axis, the body angle off-set 62 was between 4.5° to about 5.5° relative to the longitudinal balloon axis. Referring to FIG. 5B, the longitudinal fiber spacing 66 on the balloon body was about 0.4 mm and the hoop fiber spacing 68 was about 0.33 mm.

12. The elastomeric sheath used in prior process step 9 was manufactured by initially placing a tube of expanded polytetrafluoroethylene (ePTFE) over a mandrel. The ePTFE tube was extruded and expanded by stretching in the direction of the longitudinal axis of the tube; it had a wall thickness of about 0.013 mm, an outer diameter of about 1.35 mm, a mean fibril length of about 30 micrometers and was about 25 cm long. The longitudinally extruded and expanded tube had a relative high degree of longitudinal strength and has a relatively low degree of radial strength. Such a tube will therefore expand radially and resist longitudinal extension. The mandrel was slightly undersized to the tube inner diameter. The undersized mandrel had an outer diameter of about 1.34 mm. After placing the tube onto the mandrel, the tube was hand smoothed to remove any wrinkles. One end of the tube protruded over one end of the mandrel and the overhanging tube end was twisted to help secure the tube onto the mandrel.

13. The mandrel and surrounding tube were then dipped and imbibed into an elastomer solution. A solution of BioSpan® (segmented polyurethane, 24%±2% solids content; from PTG Medical LLC, part number FP70001, Berkeley Calif. 94710) was diluted with dimethylacetamide (DMAC; from Sigma-Aldrich, part number D5511, St. Louis Mo.) to about 12% (weight percent) solids content. This solution was preheated to about 60° C. in 20 cm long by 1.3 cm diameter test tube. The test tube with the preheated solution was then fixtured into a dipping fixture. The dipping fixture comprised a servo-driven, vertical cross-head with a clamping device suited to clamp and hold the mandrel in a vertical position (with the wrapped end of the tube pointing down). The servo-driven cross-head then descended and progressively submerged the mandrel and tube into the elastomer solution. The descent rate was about 0.6 cm/second. About 15 cm of the tube was submerged and held in the submerged position for a dwell time of about 30 seconds. The cross-head was then raised with an assent rate of about 0.3 cm/second until the lower end of the mandrel and tube was removed from the elastomeric solution and test tube.

14. The mandrel with the dipped tube was then removed from the dipping fixture and placed into an air convection oven. The mandrel with the dipped tube was then pre-cured at about 65° C. for about 2 minutes.

15. The mandrel and tube were then re-dipped and imbibed according to the previous step 13.

16. The mandrel and dipped tube were then pre-cured according to the previous step 14.

17. The mandrel and tube were then re-dipped and imbibed according to the previous step 13.

18. The mandrel and dipped tube were then pre-cured according to the previous step 14.

19. The mandrel and tube were then re-dipped and imbibed according to the previous step 13.

20. The mandrel and dipped tube were then removed from the dipping fixture and placed into an air convection oven. The mandrel and dipped tube were then final-cured at about 65° C. for about 60 minutes. The resulting elastomeric tube formed a sheath that was radially expandable and resisted longitudinal stretching.

21. The final cured tube/sheath was then removed from the mandrel, and cut to a length that approximated the length of the balloon. The sheath was cut to a length of about 90 mm.

22. The elastomeric sheath was then inverted. Since the elastomeric layers were built up on the external surface of the starting ePTFE thin walled tube, the inner surface of the sheath had a lubricious, primarily ePTFE surface. By inverting the sheath, the lubricious surface was now on the exterior of the sheath. The inverted sheath was then placed over the fiber reinforced balloon according to process step 9 above.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A medical device, comprising:
a catheter;
a balloon, comprising a length and a longitudinal axis and having a first end portion and a second end portion;
a first continuous fiber wrapped about the balloon, wherein said first continuous fiber traverses said length of the balloon at least several times at an angular offset from about 1° to about 45° relative to said longitudinal axis of the balloon;
wherein a traverse of said length reverses direction with regards to the longitudinal axis at a turnaround point, and wherein the location of at least two turnaround points at the second end portion vary along the longitudinal axis.

2. The medical device of claim 1, further comprising an elastomeric sheath at least partially surrounding the balloon, wherein the sheath has a degree of radial strength and a higher degree of longitudinal strength.

3. The medical device of claim 2, wherein the sheath comprises expanded polytetrafluoroethylene.

4. The medical device of claim 1, wherein the first continuous fiber is selected from the group consisting of polyethylene fiber, polyimide fiber, liquid crystal polymer fiber, carbon based fiber, metal fiber, alloy fiber, and combinations thereof.

5. The medical device of claim 2, wherein the sheath has first and second end portions and the first end portion is attached to a proximal end of the balloon and the second end portion is attached to a distal end of the balloon.

6. The medical device of claim 2, wherein said catheter has a proximal end portion and a distal end portion, wherein the sheath is attached to at least the proximal end portion of the catheter.

7. The medical device of claim 1, further comprising a second continuous fiber wrapped about the balloon, in contact with the first continuous fiber in a circumferential configuration.

8. The medical device of claim 1, wherein said continuous fiber is selected from the group consisting of polyethylene fiber, polyimide fiber, liquid crystal polymer fiber, carbon based fiber, metal fiber, alloy fiber, and combinations thereof.

9. A medical device, comprising:
a balloon having longitudinal axis;
a first continuous fiber wrapped about the balloon, wherein said first continuous fiber traverses the balloon at least several times at an angular offset from about 1° to about 45° relative to said longitudinal axis of the balloon; and
wherein a traverse of said balloon comprises the first continuous fiber extending from a first end portion of the balloon to a second end portion of the balloon and reversing direction with regards to the longitudinal axis at the second end portion to then traverse said balloon again, wherein the first continuous fiber reverses direction with regards to the longitudinal as at the second end portion at two or more positions along the longitudinal axis; and
a second continuous fiber wrapped about the balloon and substantially aligned with a perpendicular axis of the balloon, wherein the first and second fiber have different cross-sectional shapes.

10. The medical device of claim 9, wherein the first fiber has a substantially circular cross-section.

11. The medical device of claim 9, wherein the second fiber has a substantially non-circular cross-section.

12. The medical device of claim 9, wherein the first and second fiber are selected from the group consisting of polyethylene fiber, polyimide fiber, liquid crystal polymer fiber, carbon based fiber, metal fiber, alloy fiber, and combinations thereof.

13. The medical device of claim 9, further comprising:
an elastomeric sheath at least partially surrounding the medical balloon.

14. A medical device, comprising:
a catheter having a proximal and distal end;
a balloon having a body portion and mounted at the distal end of the catheter, wherein the distal end includes a port for inflation of the balloon;
a continuous fiber extending from a first end portion of the balloon to a second end portion of the balloon and back to first end portion at least several times, wherein said continuous fiber along the body portion defines an angular offset from about 1° to about 45° relative to said longitudinal axis of the balloon thus defining a first pattern and extending substantially perpendicular to a longitudinal axis of the balloon defining a second pattern wherein the continuous fiber has at least two turnaround points at which the continuous fiber reverses direction with regards to the longitudinal axis located at the second end portion, wherein the location of the at least two turnaround points at the second end portion vary along the longitudinal axis; and an elastomeric sheath at least partially surrounding a circumference of the balloon.

15. The medical device of claim 14, wherein the sheath has a low degree of radial strength and high degree of longitudinal strength.

16. The medical device of claim 15, wherein the sheath comprises expanded polytetrafluoroethylene.

17. The medical device of claim 14, wherein the continuous fiber is selected from the group consisting of polyethylene fiber, polyimide fiber, liquid crystal polymer fiber, carbon based fiber, metal fiber, alloy fiber, and combinations thereof.

18. The medical device of claim 14, wherein the sheath has a first and second end portions and the first end portion is attached to a proximal end of the balloon and the second end portion is attached to a distal end of the balloon.

19. The medical device of claim 14, wherein the fiber is selected from the group consisting of polyethylene fiber, polyimide fiber, liquid crystal polymer fiber, carbon based fiber, metal fiber, alloy fiber, and combinations thereof.

20. The medical device of claim 14, wherein the first pattern is substantially aligned to a longitudinal axis of the balloon.

21. A medical device, comprising:
a catheter having a proximal and distal end and extending along a longitudinal axis;
a balloon having two opposed shoulder portions terminating into first and second legs, wherein the balloon is arranged over a portion of the distal end of the catheter; an
a continuous fiber extending from the first leg at a first position to a second leg at a second position, the fiber being at least partially wrapped around the second leg at the second position and reversing direction with regards to the longitudinal axis and returning back to the first leg portion at a third position, wherein the first and third positions vary along the longitudinal axis.

22. The medical device of claim 21, wherein the first position is proximal to the first leg.

23. The medical device of claim 21, wherein the first position is distal to the first leg.

24. A method of making a medical balloon, comprising the steps of:
supplying a catheter having a balloon with an external surface;
attaching a first continuous fiber to the balloon external wherein said first continuous fiber traverses a length of the balloon at least several times at an angular offset from about 1° to about 45° relative to said longitudinal axis of the balloon,
wherein a traverse of said length comprises the first continuous fiber extending from a first end portion of the balloon to a second end portion of the balloon and reversing direction with regards to the longitudinal axis at the second end portion to then traverse said length again, wherein the first continuous fiber turns around at the second end portion at two or more positions along the longitudinal axis; and
surrounding the balloon with a sheath.

25. The method of claim 24, further comprising the step of attaching the sheath to the balloon external surface.

26. The medical device of claim 1, wherein said angular offset is about 1° to about 10°.

27. The medical device of claim 26, wherein said angular offset is about 4.5° to about 5.5°.

28. The medical device of claim 9, wherein said angular offset is about 1° to about 10°.

29. The medical device of claim 28, wherein said angular offset is about 4.5° to about 5.5°.

30. The medical device of claim 14, wherein said angular offset is about 1° to about 10°.

31. The medical device of claim 30, wherein said angular offset is about 4.5° to about 5.5°.

32. The medical device of claim 24, wherein said angular offset is about 1° to about 10°.

33. The medical device of claim 32, wherein said angular offset is about 4.5° to about 5.5°.

34. A medical device comprising:
a balloon having a body portion and at least one leg;
the balloon body portion having a longitudinal axis and a length parallel to the longitudinal axis;
a single continuous fiber in contact with and at least partially looping around the balloon leg before reversing direction with regards to the longitudinal axis at a turnaround point to re-traverse the body portion length;
wherein the location of at least two turnaround points at the balloon leg vary along the longitudinal axis; and
the single fiber defining, along the body portion length, an angular offset from about 1° to about 45° relative to said longitudinal axis of the balloon.

35. The medical device of claim 34, wherein said angular offset is about 1° to about 10°.

36. The medical device of claim 35, wherein said angular offset is about 4.5° to about 5.5°.

37. The medical device of claim 34, wherein said continuous fiber is selected from the group consisting of polyethylene fiber, polyimide fiber, liquid crystal polymer fiber, carbon based fiber, metal fiber, alloy fiber, and combinations thereof.

* * * * *